United States Patent [19]

Wilkerson

[11] Patent Number: 4,652,582

[45] Date of Patent: Mar. 24, 1987

[54] ANTIINFLAMMATORY-2-HALO-4,5-DIARYLPYRROLES

[75] Inventor: Wendell W. Wilkerson, Newcastle, Del.

[73] Assignee: E. I. Du Pont de Nemours and Company, Wilmington, Del.

[21] Appl. No.: 690,091

[22] Filed: Jan. 9, 1985

[51] Int. Cl.$^4$ .................. A61K 31/40; C07D 207/34; C07D 207/35; C07D 207/416
[52] U.S. Cl. ............................... 514/427; 546/281; 548/530; 548/531; 548/542; 548/560
[58] Field of Search .................. 548/560; 514/427

[56] References Cited

U.S. PATENT DOCUMENTS

| 4,267,184 | 5/1981 | Cherkofsky | 546/280 X |
| 4,267,190 | 5/1981 | Cherkofsky | 514/427 |
| 4,318,917 | 3/1982 | Cherkofsky et al. | 514/427 |
| 4,326,881 | 4/1982 | Ueda et al. | 71/95 |
| 4,335,136 | 1/1982 | Cherkofsky | 514/427 |
| 4,477,463 | 10/1984 | Cherkofsky | 548/560 X |
| 4,495,196 | 1/1985 | Boswell, Jr. | 514/427 |
| 4,503,065 | 3/1985 | Wilkerson | 514/396 |

FOREIGN PATENT DOCUMENTS

| 42-25888 | 12/1967 | Japan | 548/560 |
| 0042833 | 10/1972 | Japan | 548/560 |
| J5-9078/153-A | 5/1984 | Japan | |
| 1127927 | 9/1968 | United Kingdom | 548/560 |

OTHER PUBLICATIONS

J. Szmuszkovicz et al., *J. Med. Chem.*, 9, 527–36 (1966).
E. Aiello et al., *J. Heterocycl. Chem.*, 19(4), 977–979 (1982).

*Primary Examiner*—Joseph Paul Brust

[57] ABSTRACT

Antiinflammatory 2-halo-4,5-diarylpyrroles are provided. These pyrroles have the formula:

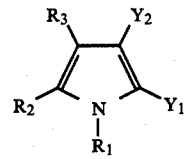

wherein
$Y_1$ is F, Cl, Br, or I;
$Y_2$ is H, Cl, or Br;
$R_1$ is H, $CH_3$, $C_2H_5$, acetyl, or

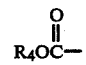

where $R_4$ is methyl, ethyl, t-butyl, or benzyl;
$R_2$ is pyridyl or

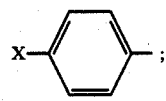

$R_3$ is pyridyl or

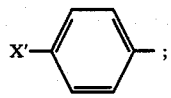

X and X' are independently H, F, Cl, Br, $OR_5$, or $R_5S(O)_n$ where n is 0, 1 or 2 and $R_5$ is $C_1$–$C_2$ alkyl; provided that one of $R_2$ or $R_3$ must be

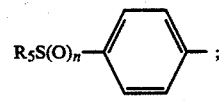

or a pharmaceutically suitable salt thereof.

Intermediates to the above pyrroles are provided where $R_1$ in the above formula is replaced by $R^1$ which is benzenesulfonyl or 4-toluenesulfonyl.

30 Claims, No Drawings

ANTIINFLAMMATORY-2-HALO-4,5-DIARYLPYRROLES

BACKGROUND OF THE INVENTION

1. Field of Invention

This invention relates to pyrrole derivatives, pharmaceutical compositions containing them and methods of using them to treat inflammation in mammals. More particularly this invention relates to antiinflammatory 2-halo-4,5-diarylpyrroles and certain intermediates for their preparation.

2. Prior Art

J. Szmuszkovicz et al, *J. Med. Chem.*, 9, 527–36 (1966) describe the synthesis and biological activity of antiinflammatory indoles and the preparation of certain diarylpyrroles.

E. Aiello et al., J. Heterocycl. Chem., 19(4), 977–979 (1982), describe the synthesis of various monobromo-, monochloro- and monoiodopyrroles as potential pharmaceutical intermediates.

Cherkofsky in U.S. Pat. No. 4,267,184 discloses the preparation of diarylpyrroles and the use of 4,5-diaryl-2-(substitutedthio)pyrroles as antiinflammatories.

U.S. Pat. No. 4,326,881 discloses 4-chloro-3-(2,3-dichlorophenyl)pyrrole and its use as a fungicide.

Japanese published Patent Appln. No. JA-7242833-R discloses β-trifluoromethylphenyl-4-halopyrroles with antibacterial activity.

Japanese published Patent Application No. J5-9078/153-A discloses 3-chloro-4-phenylpyrroles as intermediates for agrochemicals and bactericides.

Coassigned U.S. patent application Ser. No. 354,300, filed on Mar. 3, 1982, now abandoned, discloses antiinflammatory 2,3-diaryl-5-halothiophenes of the formula:

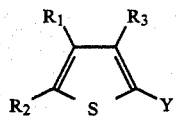

where Y is F, Cl, Br or I; $R_1$ and $R_2$ are independently pyridyl or optionally substituted phenyl; and $R_3$ is H or $C_1$–$C_2$ alkyl.

Coassigned U.S. patent application Ser. No. 404,962, filed on Aug. 3, 1982, now U.S. Pat. No. 4,503,065, discloses antiinflammatory 4,5-diaryl-2-haloimidazoles of the formula:

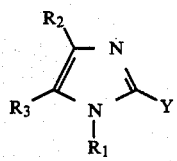

where Y is F, Cl or Br; $R_2$ and $R_3$ are pyridyl or substituted phenyl; and $R_1$ is H, methyl or 1-ethoxyethyl.

There is a continuing need for safe and effective antiinflammatory agents. Inflammation is a disease process characterized by redness, fever, swelling, and pain. Arthritis, in its various forms, is the most prevalent, chronic, and severe of the inflammatory diseases. Traumatic injury and infection also involve inflammation, and antiinflammatory drugs are often used in their treatment. The usefulness of most commercial antiinflammatories is limited because of toxicity and adverse side effects. Many produce gastric irritation and other effects, such as changes in blood cells and the central nervous system. Adrenocortical steroids produce gastric irritation and suppression of normal adrenal function.

The present invention results from efforts to develop new antiarthritic compounds with good antiinflammatory activity and minimal side effects that could be more effective in treating arthritis than presently available drugs.

SUMMARY OF THE INVENTION

According to the present invention there is provided a compound of Formula (I) useful for the treatment of inflammation in mammals:

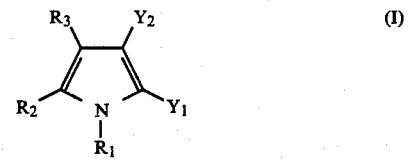

wherein
$Y_1$ is F, Cl, Br, or I;
$Y_2$ is H, Cl, or Br;
$R_1$ is H, $CH_3$, $C_2H_5$, acetyl, or

where $R_4$ is methyl, ethyl, t-butyl, or benzyl;
$R_2$ is pyridyl or

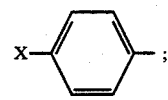

$R_3$ is pyridyl or

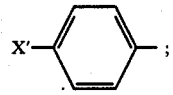

X and X' are independently H, F, Cl, Br, $OR_5$, or $R_5S(O)_n$ where n is 0, 1 or 2 and $R_5$ is $C_1$–$C_2$ alkyl; provided that one of $R_2$ or $R_3$ must be

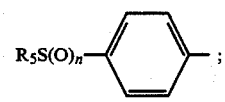

or a pharmaceutically suitable salt thereof.

There is further provided an intermediate compound for preparing a compound of Formula (I), the intermediate compound having the Formula (I'):

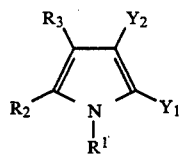
(I')

wherein $Y_1$, $Y_2$, $R_2$ and $R_3$ are as defined for Formula (I) and $R^1$ is benzenesulfonyl or 4-toluenesulfonyl.

Also provided are pharmaceutical compositions comprising a suitable pharmaceutical carrier and a compound of Formula (I), and methods of using the compounds of Formula (I) to treat inflammation.

PREFERRED EMBODIMENTS

Preferred compounds of Formula (I) are those where:
(a) one of X and X' is F, and the other is $R_5S(O)_n$ where n is 2; or
(b) $R_1$ is H or $CH_3$; or
(c) $Y_1$ is Br or Cl and $Y_2$ is H, Cl or Br.

Most preferred are those Formula (I) compounds where:
(a) $R_2$ is

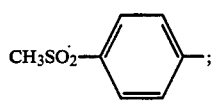

(b) $R_3$ is

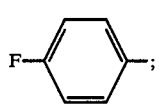

(c) $R_1$ is H or $CH_3$;
(d) $Y_1$ is Br or Cl; and
(e) $Y_2$ is H, Cl or Br.

Compounds specifically preferred because of their biological activity are:
(a) 1-Methyl-2-bromo-4-(4-fluorophenyl)-5-(4-methylsulfonylphenyl)pyrrole;
(b) 2,3-Dibromo-4-(4-fluorophenyl)-5-(4-methyllsulfonylphenyl)pyrrole;
(c) 2,3-Dichloro-4-(4-fluorophenyl)-5-(4-methylsulfonylphenyl)pyrrole; and
(d) 2-Chloro-4-(4-fluorophenyl)-5-(4-methylsulfonylphenyl)pyrrole.

DETAILED DESCRIPTION OF THE INVENTION

Synthesis

The compounds of Formula (I), where $Y_1$ is Cl, Br or I, can be prepared as shown in Scheme (1) by reacting a 2,3-diarylpyrrole of Formula (II) with one equivalent of a N-halosuccinimide such as N-chlorosuccinimide, N-bromosuccinimide or N-iodosuccinimide in a solvent such as N,N-dimethylformamide, tetrahydrofuran or dimethoxyethane. The reaction temperature can range from −78° C. to the reflux temperature of the solvent.

Scheme (1)

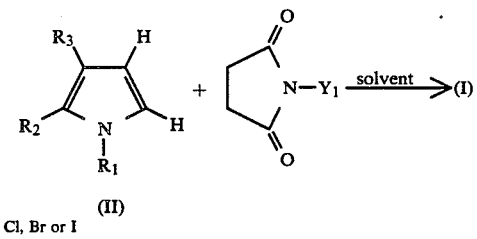

Y = Cl, Br or I

Alternatively, compounds of Formula (I) can be prepared as in Scheme (2) by treating an N-protected-2,3-diarylpyrrole (III; $R_1$=acetyl, benzenesulfonyl, 4-toluenesulfonyl or $$R_4O-\overset{O}{\underset{\|}{C}}-)$$

with a halosuccinimide. The resulting N-protected-2-halo-4,5-diarylpyrrole (IV) can be deprotected to give the compounds of Formula I ($R_1$=H; $Y_1$=Cl, Br, or I). The pyrrole where $R_1$=acetyl, benzenesulfonyl or 4-toluenesulfonyl or $R_4$=methyl or ethyl can be deprotected by alkaline hydrolysis. Where $R_4$=tert-butyl or benzyl, deprotection can be accomplished by said hydrolysis.

Scheme (2)

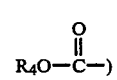

The 2,3-diarylpyrroles of Formula (II) can be prepared by methods known in the art as described in Cherkofsky, U.S. Pat. No. 4,267,184.

Compounds of Formula (I), where $Y_1$ is F, can be prepared as in Scheme (3) by treating a 2-chloro, 2-bromo- or 2-iodo-diarylpyrrole (Ia; $Y_1$=Cl, Br, or I) with a metal fluoride ($M^+F^-$) such as but not limited to silver fluoride or potassium fluoride, in a solvent such as but not limited to acetonitrile or sulfolane at temperatures ranging from 0° C. to the reflux temperature of the solvent.

Scheme (3)

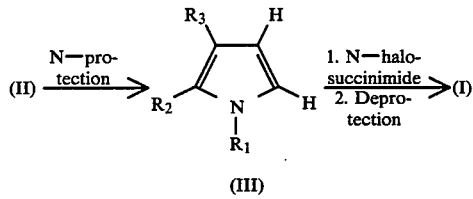

Compounds of Formula (I) where $Y_2$ is Br or Cl can be prepared as shown in Scheme (4) by reacting a 2-halo-4,5-diarylpyrrole with one equivalent of N-bromoor N-chlorosuccinimide. When $Y_1=Y_2=Cl$ or Br, then a pyrrole of Formula (II) can be reacted as shown in Scheme (5) with two equivalents of the appropriate N-halosuccinimide. In all cases $R_1$ can be H, alkyl or a nitrogen protecting group which may or may not be removed.

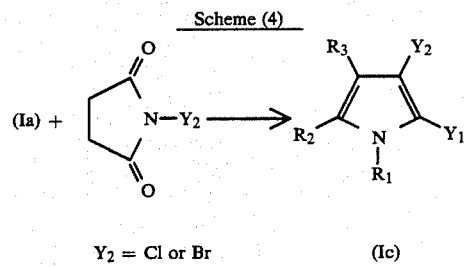

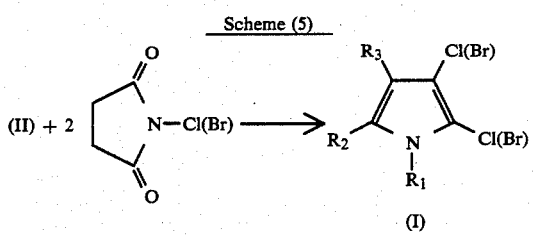

Compounds of Formula (I) where $R_1$ is $CH_3$ or $C_2H_5$ may also be prepared by reacting the corresponding compound of Formula (I) where $R_1$ is H with a base such as sodium hydride in a solvent such as N,N'-dimethylformamide, tetrahydrofuran or glyme, followed by alkylation with an alkyl halide or sulfonate such as methyl iodide or ethyl iodide as shown in Scheme (6).

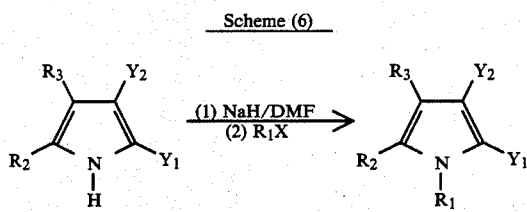

The compounds of the invention and their synthesis are further illustrated by the following examples. All temperatures are in degrees Centigrade and parts and percentages by weight.

PREPARATION 1

1-(4-Toluenesulfonyl)-2-(4-methylsulfonylphenyl)-3-(4-fluorophenyl)-1H-pyrrole

A solution of 2-(4-methylsulfonylphenyl)-3-(4-fluorophenyl)-1H-pyrrole (31.6 g, 0.1 mole) in 200 ml dry N,N'-dimethylformamide was cooled in an ice bath and treated with sodium hydride (2.4 g, 0.1 mole). The mixture was stirred for one hour and reacted with toluenesulfonyl chloride (19.0 g, 0.1 mole). The mixture was stirred at room temperature and poured into one liter of cold water with vigorous stirring. The resulting precipitate was collected by filtration, washed with water and dried. The off white solid was triturated with 150 ml chloroform, washed with other and dried. The product was collected in 100% yield (46.9 g); m.p. 228.5°–229°.

PREPARATION 2

1-tert-Butyloxycarbonyl-2-(4-methylsulfonylphenyl)-3-(4-fluorophenyl)pyrrole

A suspension of 2-(4-methylsulfonylphenyl)-3-(4-fluorophenyl)-1H-pyrrole (31.5 g, 0.1 mole) in 200 ml acetonitrile was treated with N,N'-dimethylaminopyridine (1.2 g, 0.01 mole) and di-tert-butyl-dicarbonate (26.2 g, 0.12 mole). The mixture was stirred at room temperature until no starting pyrrole was evidenced by tlc (toluene-ethyl acetate, 3:2). The mixture was poured into a liter of water and triturated. The resulting solid was collected by filtration, washed with water and dried. The product was collected in 98% yield (40.6 g); m.p. 262°–262.5°.

PREPARATION 3

1-Acetyl-2-(4-methylsulfonylphenyl)-3-(4-fluorophenyl)pyrrole

A suspension of sodium hydride (2.64 g, 0.11 mole) in 100 ml dry N,N'-dimethylformamide was heated dropwise with a solution of 2-(4-methylsulfonylphenyl)-3-(4-fluorophenyl)-1H-pyrrole (31.56 g, 0.1 mole) in 200 ml dry N,N'-dimethylformamide and stirred for one hour at room temperature. The mixture was then treated dropwise with acetyl chloride (7.9 g, 0.1 mole). The mixture was stirred for three hours and concentrated in vacuo. The residue was triturated with water, collected by filtration, dried, and column chromatographed on silica gel with toluene-ethyl acetate (3:2) as the mobile phase. The product was collected in 25% yield; m.p. 211°–214°.

PREPARATION 4

1-(4-Toluenesulfonyl)-2-bromo-4-(4-fluorophenyl)-5-(4-methylsulfonylphenyl)pyrrole A solution of 1-(4-toluenesulfonyl)-2-(4-methylsulfonylphenyl)-3-(4-fluorophenyl)pyrrole (10.0 g, 0.021 mole) in 100 ml tetrahydrofuran was cooled in an ice bath and treated with N-bromosuccinimide (3.8 g, 0.021 mole) and stirred for five hours. The mixture was diluted with one liter of water and the resulting solid was collected by filtration, washed with water and dried. The crude product was recrystallized from ethyl acetate/hexane to yield 10.0 g (87% yield); m.p. 207°–207.5°.

EXAMPLE 1

1-tert-Butyloxycarbonyl-2-bromo-4-(4-fluorophenyl)-5-(4-methylsulfonylphenyl)pyrrole A suspension of 1-tert-butyloxycarbonyl-2-(4-methylsulfonylphenyl)-3-(4-fluorophenyl)pyrrole (13.5 g, 0.032 mole) in 100 ml N,N'-dimethylformamide was treated with a solution of N-bromosuccinimide (5.7 g, 0.032 mole) in 50 ml N,N'-dimethylformamide. The mixture was stirred for four hours at room temperature and poured into a mixture of 500 ml 5% sodium bicarbonate and 500 g of ice. The resulting solid was collected by filtration, washed with water, and dried. The crude product was recrystallized from diethyl ether/hexanes to yield 11.0 g (68%); m.p. 121° dec.

EXAMPLE 2

2-Bromo-4-(4-fluorophenyl)-5-(4-methylsulfonylphenyl)-1H-pyrrole

Method A

A solution of 2-(4-methylsulfonylphenyl)-3-(4-fluorophenyl)-1H-pyrrole (31.5 g, 0.1 mole) in 200 ml N,N'-dimethylformamide was cooled in an ice bath and treated dropwise over an hour with a solution of N-bromosuccinimide (18.0 g, 0.1 mole) in 100 ml N,N-dimethylformamide. The reaction mixture was stirred in the ice bath until no starting material remained as evidenced by thin-layer chromatography (toluene-ethyl acetate, 3:2). The reaction mixture was diluted with one liter of cold water. The resulting solid was collected by filtration, washed with 5% sodium bicarbonate and water, and air dried to yield 41.5 g (100%) as the monohydrate. An analytical sample was recrystallized from 2-propanol to give the title compound as anhydrous tan crystals; m.p. 169°–170° dec.

Anal calcd. for $C_{17}H_{13}BrFNO_2S$: C, 51.78; H, 3.32; N, 3.55; S, 8.13. Found: C, 51.83; H, 3.43; N, 3.68; S, 8.27.

Method B

A solution of 1-tert-butyloxycarbonyl-2-bromo-4-(4-fluorophenyl)-5-(4-methylsulfonylphenyl)pyrrole (4.94 g, 0.01 mole) in 25 ml methylene chloride was stirred in an ice bath with 5 ml trifluoroacetic acid. The mixture was stirred in the ice bath until no starting material remained as evidenced by tlc (toluene-ethyl acetate 3:2). The mixture was made alkaline with a solution of 5% sodium bicarbonate, triturated, and the resulting solid collected by filtration, washed with water, and dried in vacuo to yield 3.8 g (96%); m.p. 168°–170°.

Method C

A solution of 1-(4-toluenesulfonyl)-2-bromo-4-(4-fluorophenyl)-5-(4-methylsulfonyl)pyrrole (4.7 g, 0.01 mole) in 25 ml ethanol and 25 ml tetrahydrofuran was treated with potassium hydroxide hydrofuran was treated with potassium hydroxide (1.0 g, 0.018 mole) and stirred at room temperature until no starting material remained as evidenced by tlc (toluene-ethyl acetate, 3:2). The mixture was concentrated in vacuo, and the residue was triturated with 100 ml water. The resulting solid was collected by filtration, washed with water and a small amount of diethyl ether, and dried in vacuo to yield 3.0 g (76%); m.p. 168°–170°.

Method D

A solution of 1-acetyl-2-bromo-4-(4-fluorophenyl)-5-(4-methylsulfonylphenyl)pyrrole (2.18 g, 0.005 mole) in 25 ml ethanol was treated with potassium hydroxide (0.56 g, 0.01 mole) and 10 ml water. The mixture was stirred at room temperature until no starting material was evidenced by tlc (toluene-ethyl acetate, 3:2). The mixture was concentrated in vacuo and the residue was triturated with water. The resulting solid was collected by filtration, washed with water, and dried in vacuo to yield 1.9 g (96%); m.p. 168°–170°.

EXAMPLE 3

2-Chloro-4-(4-fluorophenyl)-5-(4-methylsulfonylphenyl)-1H-pyrrole

By substituting N-chlorosuccinimide in the procedure of Example 2A, the title compound was obtained in 95% yield; m.p. 206°–208°.

EXAMPLE 4

2-Iodo-4-(4-fluorophenyl)-5-(4-methylsulfonylphenyl)-1H-pyrrole

By substituting N-iodosuccinimide in the procedure of Example 2A, the title compound was obtained in 25% yield after column chromatography on silica gel (toluene-ethyl acetate, 3:2); m.p. 229°–231°.

EXAMPLE 5

1-Methyl-2-bromo-4-(4-fluorophenyl)-5-(4-methylsulfonylphenyl)pyrrole

Method A: A solution of 1-methyl-2-(4-methylsulfonylphenyl)-3-(4-fluorophenyl)pyrrole (16.0 g, 0.049 mole) in 100 ml N,N'-dimethylformamide was cooled in an ice bath and reacted with N-bromosuccinimide (8.7 g, 0.049 mole). The mixture was stirred in the ice bath for one hour and at room temperature for three hours. The mixture was then diluted with 500 ml of water. The resulting solid was collected by filtration, washed with hot water and dried in vacuo to yield 19.0 g (96%); m.p. 195°–198°.

Method B

A mixture of 2-bromo-4-(4-fluorophenyl)-5-(4-methylsulfonylphenyl)-1H-pyrrole (prepared by any of the Methods of Example 2) (10.0 g, 0.025 mole) and sodium hydride (0.7 g, 0.029 mole) in 75 ml dry N,N'-dimethylformamide was stirred in an ice bath for 30 minutes and reacted with methyl iodide (4.1 g, 0.029 mole) dissolved in 25 ml of dry N,N'-dimethylformamide. The mixture was stirred in the ice bath for one hour and at room temperature for four hours. The reaction mixture was concentrated in vacuo, and the residue was triturated with 300 ml water. The resulting solid was collected by filtration, washed with water, and dried to yield 10.0 g (96%); m.p. 196°–197°.

EXAMPLE 6

2,3-Dibromo-4-(4-fluorophenyl)-5-(4-methylsulfonylphenyl)-1H-pyrrole

A solution of 2-bromo-4-(4-fluorophenyl)-5-(4-methylsulfonylphenyl)-1H-pyrrole (3.9 g, 0.01 mole) in 50 ml of N,N'-dimethylformamide was reacted with N-bromosuccinimide (1.8 g, 0.01 mole) and stirred at room temperature until no starting pyrrole remained. The mixture was diluted with 500 ml of cold water. The resulting precipitate was collected by filtration, washed with 5% sodium bicarbonate and water, and dried in vacuo to yield 4.7 g (100%); m.p. 247° dec.

Anal. Calcd for $C_{17}H_{12}Br_2FNO_2S$: MW 473.18: C, 43.15; H, 2.56; N, 2.96; S, 6.78. Found: C, 43.03; H, 2.61; N, 2.85; S, 6.79.

EXAMPLE 7

2-Bromo-3-chloro-4-(4-fluorophenyl)-5-(4-methylsulfonylphenyl)-1H-pyrrole

By substituting N-chlorosuccinimide in Example 6, the title compound was obtained in 98% yield; m.p. 206°–209°.

EXAMPLE 8

2-Chloro-3-bromo-4-(4-fluorophenyl)-5-(4-methylsulfonylphenyl)-1H-pyrrole

By substituting 2-chloro-4-(4-fluorophenyl)-5-(4-methylsulfonylphenyl)-1H-pyrrole in Example 6, the title compound was obtained in 97% yield; m.p. 208° dec.

EXAMPLE 9

2,3-Dichloro-4-(4-fluorophenyl)-5-(4-methylsulfonyl)phenyl)-1H-pyrrole

A solution of 2-(4-fluorophenyl)-3-(4-methylsulfonylphenyl)-1H-pyrrole (7.9 g, 0.025 mole) in 150 ml of N,N'-dimethylformamide was reacted with N-chlorosuccinimide (6.7 g, 0.05 mole) and stirred at room temperature for three hours. The reaction mixture was poured into one liter of water and triturated vigorously. The resulting solid was collected by filtration, washed with 5% sodium bicarbonate and hot water, and dried to yield 9.0 g (94%); m.p. 200° dec.

EXAMPLE 10

1-Acetyl-2-bromo-4-(4-fluorophenyl)-5-(4-methylsulfonylphenyl)pyrrole

By substituting 1-acetyl-2-(4-methylsulfonylphenyl)-3-(4-fluorophenyl)pyrrole in the procedure for Example 5A, the title compound was prepared in 25% yield after column chromatography on neutral alumina (toluene-ethyl acetate, 3:2); m.p. 121°–125°.

The compounds of Examples 1–10 and compounds which can be prepared following procedures analogous to those outlined above are known in Table I.

TABLE I

| Ex. No. | $R_3$ | $R_2$ | $R_1$ | $Y_1$ | $Y_2$ | m.p. (°C.) |
|---|---|---|---|---|---|---|
| 1 | $4\text{-}FC_6H_4$ | $4\text{-}CH_3SO_2C_6H_4$ | $t\text{-}Bu\text{-}O\text{-}C\!=\!O$ | Br | H | 121° dec |
| 2 | $4\text{-}FC_6H_4$ | $4\text{-}CH_3SO_2C_6H_4$ | H | Br | H | 169–170° dec. |
| 3 | $4\text{-}FC_6H_4$ | $4\text{-}CH_3SO_2C_6H_4$ | H | Cl | H | 206–208° |
| 4 | $4\text{-}FC_6H_4$ | $4\text{-}CH_3SO_2C_6H_4$ | H | I | H | 229–231° |
| 5 | $4\text{-}FC_6H_4$ | $4\text{-}CH_3SO_2C_6H_4$ | $CH_3$ | Br | H | 195–198° |
| 6 | $4\text{-}FC_6H_4$ | $4\text{-}CH_3SO_2C_6H_4$ | H | Br | Br | 247° dec. |
| 7 | $4\text{-}FC_6H_4$ | $4\text{-}CH_3SO_2C_6H_4$ | H | Br | Cl | 206–209° |
| 8 | $4\text{-}FC_6H_4$ | $4\text{-}CH_3SO_2C_6H_4$ | H | Cl | Br | 208° dec. |
| 9 | $4\text{-}FC_6H_4$ | $4\text{-}CH_3SO_2C_6H_4$ | H | Cl | Cl | 200° dec. |
| 10 | $4\text{-}FC_6H_4$ | $4\text{-}CH_3SO_2C_6H_4$ | $CH_3\text{-}C\!=\!O$ | Br | H | 121–125° |
| 11 | $4\text{-}CH_3SO_2C_6H_4$ | $4\text{-}FC_6H_4$ | H | F | H | |
| 12 | $4\text{-}CH_3SO_2C_6H_4$ | $4\text{-}FC_6H_4$ | H | Cl | H | |
| 13 | $4\text{-}CH_3SO_2C_6H_4$ | $4\text{-}FC_6H_4$ | H | Br | H | |
| 14 | $4\text{-}CH_3SO_2C_6H_4$ | $4\text{-}FC_6H_4$ | H | I | H | |
| 15 | $4\text{-}CH_3OC_6H_4$ | $4\text{-}CH_3SO_2C_6H_4$ | H | Cl | H | |
| 16 | $4\text{-}CH_3OC_6H_4$ | $4\text{-}CH_3SO_2C_6H_4$ | H | Br | H | |
| 17 | $C_6H_4$ | $4\text{-}CH_3SO_2C_6H_4$ | H | Cl | H | |
| 18 | $C_6H_4$ | $4\text{-}CH_3SO_2C_6H_4$ | H | Br | H | |
| 19 | $4\text{-}ClC_6H_4$ | $4\text{-}CH_3SO_2C_6H_4$ | H | Cl | H | |
| 20 | $4\text{-}ClC_6H_4$ | $4\text{-}CH_3SO_2C_6H_4$ | H | Br | H | |
| 21 | $4\text{-}BrC_6H_4$ | $4\text{-}CH_3SO_2C_6H_4$ | H | Cl | H | |
| 22 | $4\text{-}BrC_6H_4$ | $4\text{-}CH_3SO_2C_6H_4$ | H | Br | H | |
| 23 | 2-pyridyl | $4\text{-}CH_3SO_2C_6H_4$ | H | Cl | H | |
| 24 | 2-pyridyl | $4\text{-}CH_3SO_2C_6H_4$ | H | Br | H | |
| 25 | 3-pyridyl | $4\text{-}CH_3SO_2C_6H_4$ | H | Br | H | |
| 26 | 4-pyridyl | $4\text{-}CH_3SO_2C_6H_4$ | H | Cl | H | |
| 27 | 4-pyridyl | $4\text{-}CH_3SO_2C_6H_4$ | H | Br | H | |
| 28 | $4\text{-}FC_6H_4$ | $4\text{-}CH_3SO_2C_6H_4$ | H | Cl | H | |
| 29 | $4\text{-}FC_6H_4$ | $4\text{-}CH_3SO_2C_6H_4$ | H | Br | H | |
| 30 | $4\text{-}FC_6H_4$ | $4\text{-}CH_3SO_2C_6H_4$ | H | F | Cl | |
| 31 | $4\text{-}FC_6H_4$ | $4\text{-}CH_3SC_6H_4$ | H | Br | H | |
| 32 | $4\text{-}FC_6H_4$ | $4\text{-}CH_3SOC_6H_4$ | H | Br | H | |

Bu = butyl

DOSAGE FORMS

The antiinflammatory and/or analgesic agents of this invention can be administered to treat inflammation and/or relieve pain by any means that produces contact of the active agent with the agent's site of action in the body of a mammal. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.1 to 100 milligrams per kilogram of body weight. Ordinarily 0.5 to 50, and preferably 1 to 25 milligrams per kilogram per day given in divided doses 1 to 6 times a day or in sustained release form is effective to obtain desired results.

Dosage forms (compositions) suitable for internal administration contain from about 25 milligrams to about 500 milligrams of active ingredient per unit. In these pharmaceutical compositions the active ingredient will ordinarily be present in an amount of about 0.5-95% by weight based on the total weight of the composition.

The active ingredient can be administered orally in solid dosage forms, such as capsules, tablets, and powders, or in liquid dosage forms, such as elixirs, syrups, and suspensions, it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Some of the compounds of this invention form salts. Solutions for parenteral administration of these compounds contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition parenteral solutions can contain preservatives, such as benzalkonium chloride, methyl- or propyl-paraben, and chlorobutanol.

Suitable pharmaceutical carriers are described in *Remington's Pharmaceutical Sciences*, A. Osol, a standard reference text in this field.

Useful pharmaceutical dosage forms for administration of the compounds of this invention can be illustrated as follows:

CAPSULES

A large number of unit capsules are prepared by filling standard two-piece hard gelatin capsules each with 75 milligrams of powdered active ingredient, 150 milligrams of lactose, 24 milligrams of talc, and 6 milligrams magnesium stearate.

CAPSULES

A mixture of active ingredient in soybean oil is prepared and injected by means of a positive displacement pump into gelatin to form soft gelatin capsules containing 75 milligrams of the active ingredient. The capsules are washed and dried.

TABLETS

A large number of tablets are prepared by conventional procedures so that the dosage unit is 75 milligrams of active ingredient, 6 milligrams of magnesium stearate, 70 milligrams of microcrystalline cellulose, 11 milligrams of cornstarch and 200 milligrams of lactose. Appropriate coatings may be applied to increase palatability or delay absorption.

INJECTABLE

A parenteral composition suitable for administration by injection is prepared by stirring 1.5% by weight of active ingredient in 10% by volume propylene glycol and water. The solution is sterilized by commonly used techniques.

SUSPENSION

An aqueous suspension is prepared for oral administration so that each 5 milliliters contain 25 milligrams of finely divided active ingredient, 200 milligrams of sodium carboxymethyl cellulose, 5 milligrams of sodium benzoate, 1.0 grams of sorbitol solution, U.S.P., and 0.025 milliliters of vanillin.

INJECTABLE

A parenteral composition suitable for administration by injection is prepared by dissolving 1% by weight of active ingredient in sodium chloride injection U.S.P. XX and adjusting the pH of the solution to between 6 and 7. The solution is sterilized by commonly used techniques.

USE

To detect and compare the antiinflammatory activities of compounds in this series and standard drugs, the adjuvant arthritis test was used. A good correlation exists with results in this assay and human efficacy. (*Federation Proceedings*, 32, 2, 1973 "Models Used for the Study and Therapy of Rheumatoid Arthritis'-'—Symposium of the American Society for Pharmacology and Experimental Therapeutics).

ESTABLISHED ADJUVANT-INDUCED ARTHRITIS IN RATS

Male Charles River Lewis rats (130-150 grams) are injected subcutaneously in the plantar area of the right hind paw with 0.1 ml of adjuvant (Difco heat-killed, lyophilized *Mycobacterium butyricum* suspended in mineral oil 5 mg/ml). 20 Non-arthritic controls are injected with mineral oil. The animals are held for 2 weeks to allow development of arthritis. Paw volumes (uninjected, left hind paw) are measured and the adjuvant injected rats are culled and distributed to treatment groups of 10 of equal disease severity. Non-arthritic controls are distributed to 2 groups of 10. The rats are given oral doses of compound or PVA-Acacia (Polyvinyl Alcohol 1%, Gum acacia, U.S.P. 5%, Methylparaben 0.5%) or 0.25% methocel (10 ml/kg) by gavage on that day and on the 6 following days. One day after the last dose, the paw volumes (uninjected, left hind paw) are measured using a Ugo Basile Volume Differential Meter Model 7101. Inhibiting effects are calculated by the following formula:

$$\frac{\text{Arthritic Control} \quad \text{Treatment Group}}{\text{Mean Paw Volume (ml)} - \text{Mean Paw Volume (ml)}} \times 100 =$$
$$\frac{\text{Arthritic Control} \quad \text{Non-Arthritic Control}}{\text{Mean Paw Volume (ml)} - \text{Mean Paw Volume (ml)}}$$

% Decrease from Control Mean Paw Volume.

Dose-response regression lines of the percent decrease are plotted on semi-log paper by visual fit and the effective dose for 50% decrease from control paw volume (ED50) is determined by inspection. Data for some of the compounds of this invention are summarized in Table II.

Compounds from this series were also compared to indomethacin, phenylbutazone, ibuprofen, and aspirin.

TABLE II

| Example | Adjuvant Arthritis $ED_{50}$ (mg/kg) |
|---|---|
| 1 | 44% @ 9[1] |
| 2 | 1.1 |
| 3 | 0.5 |
| 4 | 22.0 |
| 5 | 1.7 |
| 6 | 0.88 |
| 8 | 45% @ 3[1] |
| 9 | 1.5 |
| Indomethacin | 0.3 |
| Phenylbutazone | 10 |
| Ibuprofen | 100 |
| Aspirin | 305 |

[1] % decrease from control paw volume at indicated daily dose.

What is claimed is:

1. A compound having the formula:

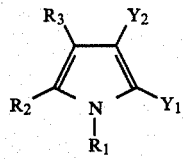

wherein
$Y_1$ is F, Cl, Br, or I;
$Y_2$ is H, Cl, or Br;
$R_1$ is H, $CH_3$, $C_2H_5$, or acetyl;
$R_2$ is

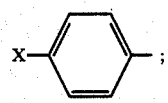

$R_3$ is

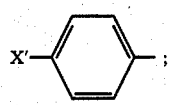

X and X' are independently H, F, Cl, Br, $OR_5$, or $R_5S(O)_n$ where n is 0, 1 or 2 and $R_5$ is $C_1$-$C_2$ alkyl; provided that one of $R_2$ or $R_3$ must be

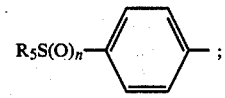

or a pharmaceutical suitable salt thereof.

2. A compound of claim 1 wherein one of X and X' is F and the other is $R_5S(O)_n$ where n is 2.
3. A compound of claim 1 wherein $R_1$ is H or $CH_3$.
4. A compound of claim 1 wherein $Y_1$ is Br or Cl and $Y_2$ is H, Cl or Br.
5. A compound of claim 1 wherein $R_2$ is

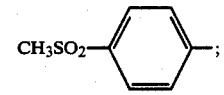

$R_3$ is

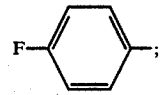

$R_1$ is H or $CH_3$; $Y_1$ is Br or Cl; and $Y_2$ is H, Cl or Br.

6. A compound of claim 1 wherein $Y_1=Y_2$ and is selected from Br or Cl.
7. The compound of claim 1 which is 1-methyl-2-bromo-4-(4-fluorophenyl)-5-(4-methylsulfonylphenyl)-pyrrole.
8. The compound of claim 1 which is 2,3-di-bromo-4-(4-fluorophenyl)-5-(4-methylsulfonylphenyl)pyrrole.
9. The compound of claim 1 which is 2,3-di-chloro-4-(4-fluorophenyl)-5-(4-methylsulfonylphenyl)pyrrole.
10. The compound of claim 1 which is 2-chloro-4-(4-fluorophenyl)-5-(4-methylsulfonylphenyl)pyrrole.
11. A pharmaceutical composition consisting essentially of a suitable pharmaceutical carrier and an effective antiinflammatory amount of at least one compound of claim 1.
12. A pharmaceutical composition consisting essentially of a suitable pharmaceutical carrier and an effective antiinflammatory amount of at least one compound of claim 2.
13. A pharmaceutical composition consisting essentially of a suitable pharmaceutical carrier and an effective antiinflammatory amount of at least one compound of claim 3.
14. A pharmaceutical composition consisting essentially of a suitable pharmaceutical carrier and an effective antiinflammatory amount of at least one compound of claim 4.
15. A pharmaceutical composition consisting essentially of a suitable pharmaceutical carrier and an effective antiinflammatory amount of at least one compound of claim 5.
16. A pharmaceutical composition consisting essentially of a suitable pharmaceutical carrier and an effective antiinflammatory amount of at least one compound of claim 6.
17. A pharmaceutical composition consisting essentially of a suitable pharmaceutical carrier and an effective antiinflammatory amount of at least one compound of claim 7.

18. A pharmaceutical composition consisting essentially of a suitable pharmaceutical carrier and an effective antiinflammatory amount of at least one compound of claim 8.

19. A pharmaceutical composition consisting essentially of a suitable pharmaceutical carrier and an effective antiinflammatory amount of at least one compound of claim 9.

20. A pharmaceutical composition consisting essentially of a suitable pharmaceutical carrier and an effective antiinflammatory amount of at least one compound of claim 10.

21. A method of treating inflammation in a mammal which comprises administering to the mammal an effective antiinflammatory amount of at least one compound of claim 1.

22. A method of treating inflammation in a mammal which comprises administering to the mammal an effective antiinflammatory amount of at least one compound of claim 2.

23. A method of treating inflammation in a mammal which comprises administering to the mammal an effective antiinflammatory amount of at least one compound of claim 3.

24. A method of treating inflammation in a mammal which comprises administering to the mammal an effective antiinflammatory amount of at least one compound of claim 4.

25. A method of treating inflammation in a mammal which comprises administering to the mammal an effective antiinflammatory amount of at least one compound of claim 5.

26. A method of treating inflammation in a mammal which comprises administering to the mammal an effective antiinflammatory amount of at least one compound of claim 6.

27. A method of treating inflammation in a mammal which comprises administering to the mammal an effective antiinflammatory amount of at least one compound of claim 7.

28. A method of treating inflammation in a mammal which comprises administering to the mammal an effective antiinflammatory amount of at least one compound of claim 8.

29. A method of treating inflammation in a mammal which comprises administering to the mammal an effective antiinflammatory amount of at least one compound of claim 9.

30. A method of treating inflammation in a mammal which comprises administering to the mammal an effective antiinflammatory amount of at least one compound of claim 10.

* * * * *